United States Patent [19]

Moore

[11] Patent Number: 5,010,254
[45] Date of Patent: Apr. 23, 1991

[54] SYSTEM FOR COMMUNICATING ENERGY BETWEEN RELATIVELY MOVING DEVICES

[75] Inventor: John F. Moore, Libertyville, Ill.

[73] Assignee: Kabushiki Kaisha Toshiba, Kanagawa, Japan

[21] Appl. No.: 333,249

[22] Filed: Apr. 5, 1989

[51] Int. Cl.[5] .............................................. G02B 27/00
[52] U.S. Cl. ........................................ 250/551; 378/10
[58] Field of Search ................... 250/551, 445 T, 490, 250/231 SE, 234–236; 378/4, 10, 15, 19; 340/552

[56] References Cited

U.S. PATENT DOCUMENTS

| 4,220,863 | 9/1980 | McBride et al. | 378/10 |
| 4,246,484 | 1/1981 | Fetter | 378/10 |
| 4,377,867 | 3/1983 | Oliver | 378/19 |
| 4,578,801 | 3/1986 | Oliver | 378/19 |
| 4,769,828 | 9/1988 | LeMay | 378/10 |
| 4,796,183 | 1/1989 | Ermert et al. | 378/15 |

Primary Examiner—David C. Nelms
Assistant Examiner—Stephone B. Allen
Attorney, Agent, or Firm—Finnegan, Henderson, Farabow, Garrett and Dunner

[57] ABSTRACT

A system is provided for communicating energy from one device, such as the rotating frame of a CT scanner, to another device, such as the fixed frame of a CT scanner, where the two devices are capable of movement relative to one another. A plurality of transmitting elements are mounted on one of the devices and a plurality of receiving elements are mounted on the other device, spaced equidistantly around the perimeters of the respective devices. The number of receiving elements is one different than the number of transmitting elements, and the range of operation between a transmitting element and a receiving element is sufficient to assure an operative relationship between at least one of the transmitting elements and one of the receiving elements upon the relative movement of the devices.

18 Claims, 6 Drawing Sheets

SYSTEM FOR COMMUNICATING ENERGY BETWEEN RELATIVELY MOVING DEVICES

BACKGROUND OF THE INVENTION

This invention relates to a system for communicating energy between two devices capable of relative linear or rotary motion, and more particularly, to a system for communicating data or power between a rotating frame and a fixed frame of a computed tomography ("CT") scanner.

With a conventional X-ray CT scanner, an X-ray tube is mounted on a rotating frame having a large diameter for the insertion of a patient. A radiation detector is set on the rotating frame opposite the X-ray tube to detect the radiation beams permeating the patient. The rotating frame is rotatably mounted on a fixed frame so that during operation the rotating frame and the fixed frame are in relative motion.

High-voltage power needed to operate the X-ray tube must be transmitted from the fixed frame to the rotating frame. Likewise, data collected by the radiation detector must be transmitted back from the rotating frame to the fixed frame. In addition, it is desirable that the rotating frame be able to rotate continuously.

The conventional solution is to interpose mechanical slip rings between the rotating frame and the fixed frame. Brushes mounted on the rotating frame contact the slip rings mounted on the fixed frame to allow electrical transmission of power or data. This mechanical interface, however, is subject to problems of wear and intermittent electrical contact. Furthermore, if data is transmitted at a high transmission rate, noise introduced by the electrical contacts may cause transmission errors.

An alternative solution is to use a single transmitter mounted on one of the devices, for example, the rotating frame, and a single reCeiver mounted on the other device, for example, the fixed frame, as shown in commonly-assigned application Ser. No. 07/316,991 entitled "Communication System for Transmitting Data," filed Feb. 28, 1989, and commonly-assigned application Ser. No. 07/317,026 entitled "Communication System for Transmitting Data," filed Feb. 28, 1989. With these arrangements, however, the path length between the input and the output may vary by half the circumference of the rotating frame. When transmitting data from the rotating frame of a CT scanner to the fixed frame of the CT scanner, the transmission rate may be so high that this variation in path length will cause phase errors to occur.

Multiple transmitters and receivers may be used, but this can be expensive. If many transmitters or receivers are needed, or if the effective range of operation of such transmitters and receivers must extend completely around the circumference of the rotating frame or the fixed frame, the cost is increased. Furthermore, there is a possibility of phase interference if two or more transmit-receive pairs are operating at the same time.

Similar problems arise when the transmitters and receivers are on two devices which must move laterally with respect to each other.

SUMMARY OF THE INVENTION

Accordingly, it is an object of the present invention to provide a system for communicating energy from one device, such as the rotating frame of a CT scanner, to another device, such as the fixed frame of a CT scanner, where the two devices are capable of movement relative to one another, through use of multiple transmitters and receivers, while minimizing their size and number.

It is another object of the invention to provide a system for communicating energy from one device to another device where the two devices are capable of movement relative to one another via linear motion.

It is still another object of the invention to avoid simultaneous operation of more than one transmit-receive pair, except when the relative phase difference is zero.

Additional objects and advantages of the invention will be set forth in part in the description that follows, and in part will be obvious from the description or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a system for communicating energy from a first device to a second device, where the first and second devices are capable of movement relative to one other and include corresponding first and second parallel line segments which pass by one another upon the relative movement of the devices, is provided which comprises means for transmitting energy, including a plurality of transmitting elements mounted on the first device equidistant from one another along a first length of the first line segment, and means for receiving energy from the transmitting means, including a plurality of receiving elements mounted on the second device equidistant from one another along a second length of the second line segment corresponding to the first length of the first line segment, wherein the number of receiving elements is one different than the number of transmitting elements, and wherein the range of operation between a transmitting element and a receiving element is sufficient to assure an operative relationship between at least one of the transmitting elements and one of the receiving elements upon the relative movement of the devices.

The accompanying drawings, which are incorporated in and constitute a part of this specification, illustrate several exemplary embodiments of the invention and together with the description, serve to explain the principles of the invention.

DESCRIPTION OF THE PREFERRED EMBODIMENTS

Figure 1:
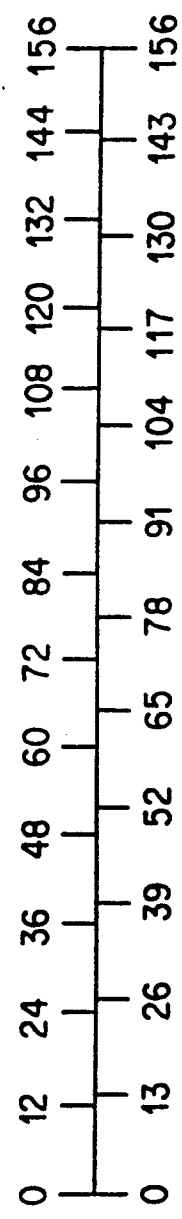
FIG. 1 is a conventional vernier diagram.

The system of the present invention is based on the vernier principle. FIG. 1 is a conventional linear vernier diagram in which a line 156 units long is divided into 12 and 13 equal parts above and below the line. As shown, the corresponding points at 0 and 156 (which can be considered as the same point if the line is wrapped in a circle) are lined up. If there is relative motion between the upper and lower scales, the points at 0 and 156 on the line will no longer line up, but points at 12 and 13 will line up if, for example, the lower scale is shifted to the left by one unit. Similarly, if the lower scale is shifted to the left by two units, the points at 24 and 26 on the line will line up.

Figure 2:
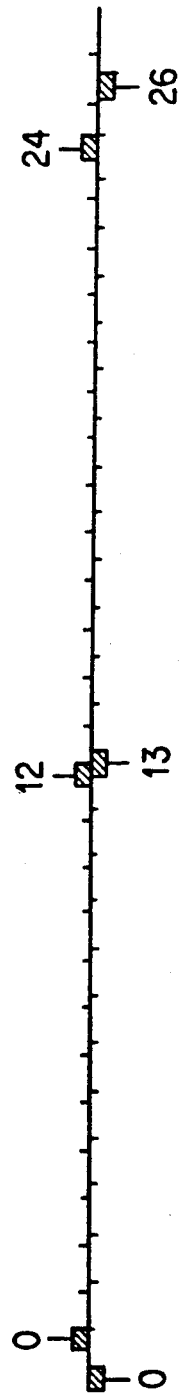
FIG. 2 shows in greater detail a portion of the linear vernier diagram of FIG. 1.

If the scale points on the line are considered to be a half unit wide, then one pair of these wider "points" will always be opposite each other, even as the scales slide continuously relative to one another. FIG. 2 shows a portion of the linear vernier diagram of FIG. 1 in greater detail where the scale points on the line are a half unit wide. As shown in FIG. 2, the "point" at 12 on the upper scale extends from 11.75 to 12.25. This "point" is lined up with the "point" at 13 on the lower scale, which extends from 12.75 to 13.25, as the scale shifts to the left.

Figure 3:
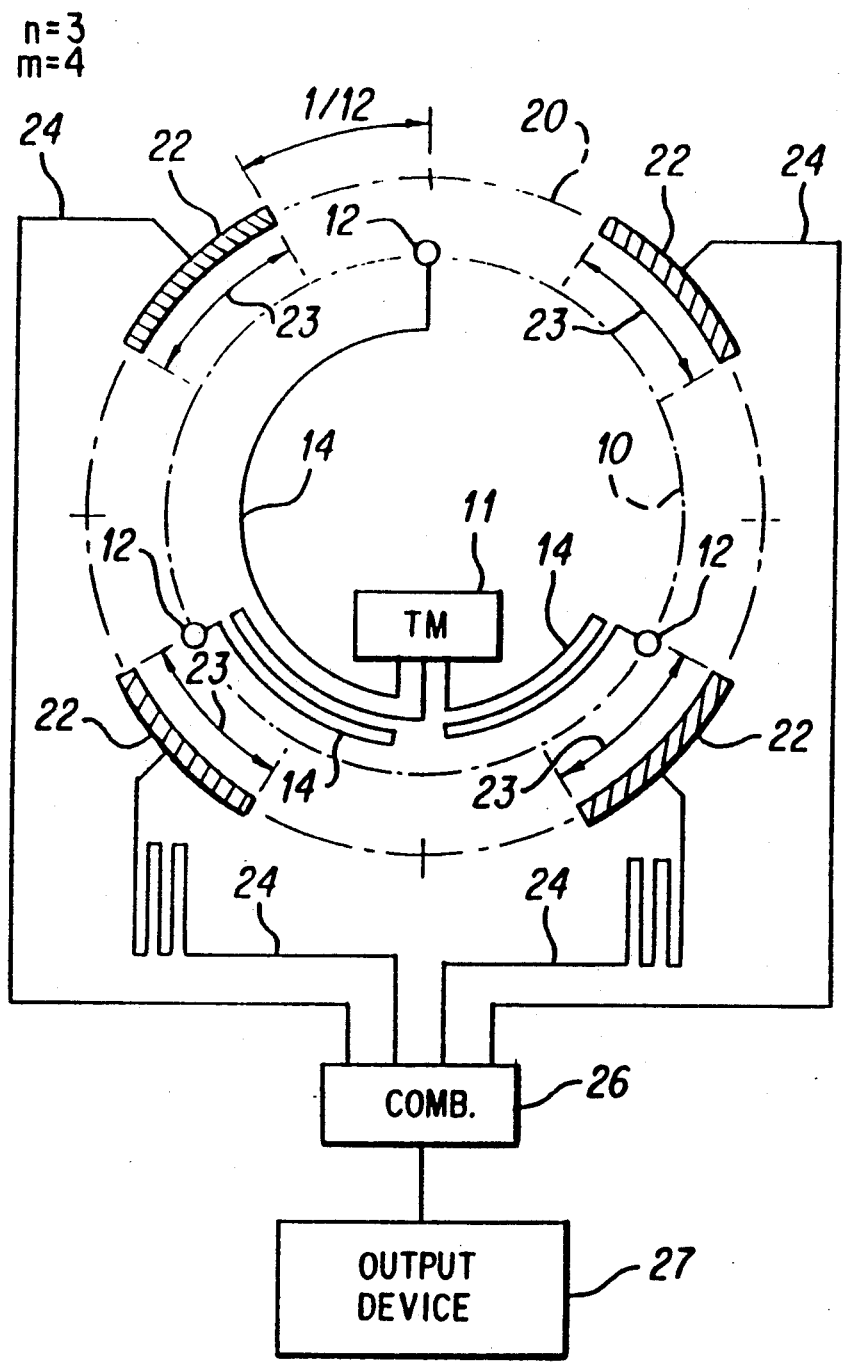
FIG. 3 represents diagrammatically a pair of relatively rotatable devices with point transmitters and extended receivers in accordance with a first embodiment of the invention.

The vernier principle, in accordance with this invention, is applied to a system for communicating energy between two large-diameter devices, such as a fixed frame and a rotating frame of a CT scanner. As represented in FIG. 3, a first large-diameter device represented by line 10 is placed inside another large-diameter device represented by line 20. Lines 10 and 20 are parallel to each other. The first device and the second device are capable of movement relative to one another in the direction of lines 10 and 20. The first device may be, for example, a rotating frame of a CT scanner, whereas the second device may be, for example, a fixed frame of the CT scanner.

In accordance with the invention, a plurality of transmitting elements are mounted on the first device equidistant from one another along a first length of a first line segement. In the embodiment of FIG. 3, transmitting elements 12 are mounted on the first device equidistant from one another along line 10. In order to transmit energy from the first device, a transmitter 11 is connected to transmitting elements 12 by transmission lines 14. The transmitting elements 12 may transmit energy in a variety of ways including, for example, electric current and/or voltage, radio waves, infrared through ultraviolet light, ultrasound, and magnetic fields.

A plurality of receiving elements are also mounted on the second device equidistant from one another along a second length of a second line segment corresponding to the first length of the first line segment. In the embodiment of FIG. 3, receiving elements 22 are mounted on the first device equidistant from one another along line 20. The receiving elements 22 are compatible with the transmitting elements 12 for receiving the energy transmitted by the transmitting elements over an operative range 23. The receiving elements 22 are connected by transmission lines 24 to a combiner 26 from which the energy received by the receiving elements is output to an output device 27.

In the embodiment shown in FIG. 3, the number of transmitting elements (n) is three, and the number of receiving elements (m) is four. Thus, the number of receiving elements is one different than the number of transmitting elements. As the first device is moved relative to the second device, the operative range 23 of at least one of the receiving elements 22 will overlap with one of the transmitting elements 12, so that the one receiving element receives energy transmitted from the one transmitting element. In this way, at least one transmit-receive pair will always be in an operative relationship for transmitting and receiving energy, even though the devices are in relative motion.

The transmitting elements 12 are driven from a common origin by connecting them with equal length transmission lines 14 to a common input at transmitter 11. Likewise, the receiving elements 22 are connected to a common collection point at combiner 26 with equal length transmission lines 24. The energy transmitted on the transmission lines 24 is combined into a single output in combiner 26, which is connected to output device 27.

In the embodiment shown in FIG. 3, the path length through which the energy must travel from the transmitter 11 to the output device 27 varies only minimally with the relative position of the devices. The path length is always the same from the transmitter 11 to the transmitting elements 12 and from the receiving elements 22 to the receiver 27. The path length between the operative transmitting element and the operative receiving element varies only by one half of the operative range 23 of the receiving element, which in this embodiment is one-twelfth of the perimeter of the second device along line 20. This can prove to be a significant advantage over using only a single transmit-receive pair in which the path length may vary by half the circumference of one of the devices. At high transmission rates of data, for example, phase errors of sufficient magnitude may occur as the path length varies in a single transmit-receive pair system. Such errors can be reduced by the system of FIG. 3.

Furthermore, by applying the vernier principle as taught in the embodiment of FIG. 3, no more than two transmit-receive pairs will be operative at any one time, and at those times, the relative phase difference between the two pairs is zero. That is, in the case where two transmit-receive pairs are operative simultaneously so that energy is transmitted over two of the transmission lines 24 to the combiner 26 (i.e., in the position of the two devices shown in FIG. 3), the path length from the transmitter 11 is the same, so that there is no phase interference at the input to the combiner 26.

In accordance with the invention, the transmitting elements may be point sources or may be extended. For example, where the transmitting elements are optical transmitting elements, they may be extended by known optical means such as light guides or diffusers. Likewise, the plurality of receiving elements may be either point receivers or may be extended. If the sources are point sources, the receivers must be extended. If the sources are extended, the receivers may be either point receivers or extended.

In the embodiment of FIG. 3, the plurality of transmitting elements 12 are point sources, and the plurality of receiving elements 22 are extended receivers. Sources 12 and receivers 22 combine to have an operative range 23. The operative range 23 is $1/(n \cdot m)$ of the perimeter of the second device alone line 20 to assure that at least one of the receivers is positioned in operative relationship with one of the sources. In the embodiment shown, where the number of sources (n) is three and the number of receivers (m) is four, the operative range 23 is one-twelfth of the perimeter of the second device along line 20. By applying the vernier principle as taught by this invention, not only are a minimum number of transmitters and receivers required, but their operative range and thus their size around the perimeters of the devices is also minimized.

Figure 4:
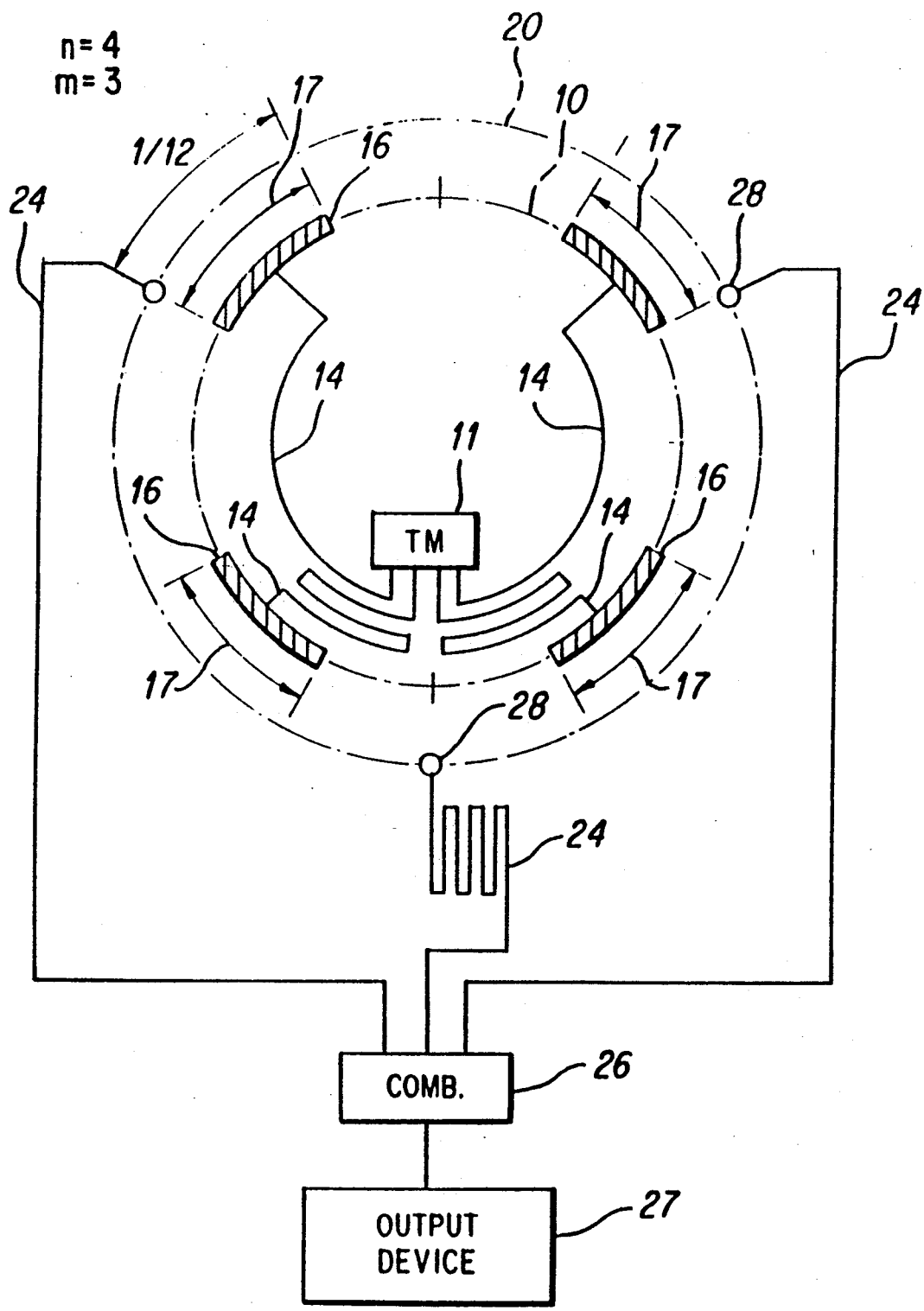
FIG. 4 represents diagrammatically a pair of relatively rotatable devices with extended transmitters and point receivers in accordance with a second embodiment of the invention.

In a second embodiment shown in FIG. 4, a plurality of extended sources 16 are mounted on the first device equidistant from one another along line 10. The sources are connected with equal length transmission lines 14 to a common input at transmitter 11. A plurality of point receivers 28 are also mounted on the second device equidistant from one another along line 20. The receivers 28 are connected to a common collection point at combiner 26 with equal length transmission lines 24. The number of receivers is one different than the number of sources.

Sources 16 and receivers 28 combine to have an operative range 17. In this second embodiment, where the transmitting elements are extended sources and the receiving elements are point receivers, the operative range is 1/(n·m) of the perimeter of the first device along line 10. Thus, where the number of sources (n) is four and the number of receivers (m) is three, the operative range is one-twelfth of the perimeter of the first device along line 10.

Figure 5:
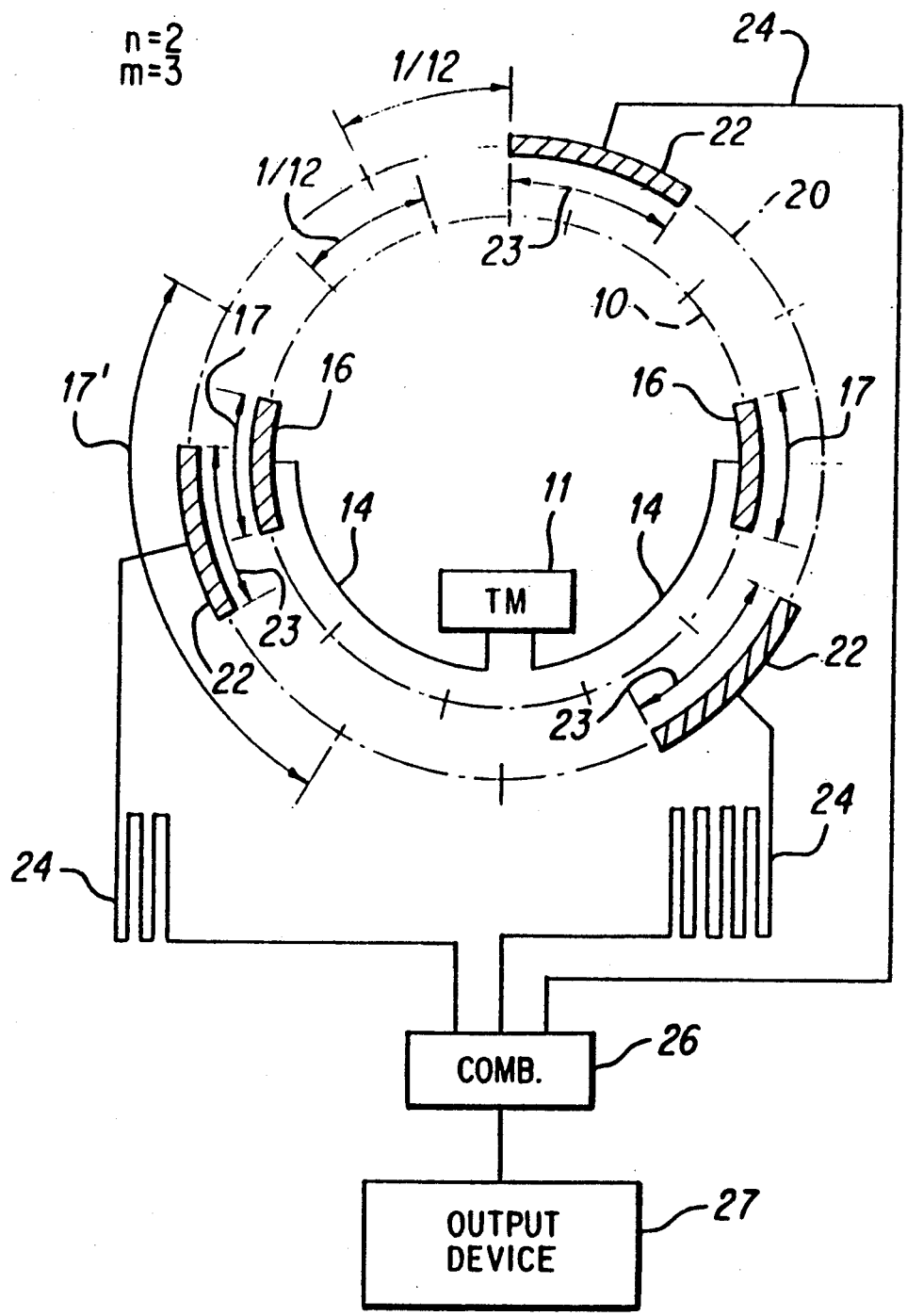
FIG. 5 represents diagrammatically a pair of relatively rotatable devices with extended transmitters and extended receivers in accordance with a third embodiment of the invention.

In a third embodiment of the invention shown in FIG. 5, a plurality of extended sources 16 are mounted on the first device equidistant from one another along line 10. The sources are connected with equal length transmission lines 14 to a common input at transmitter 11. A plurality of extended receivers 22 are also mounted on the second device equidistant from one another along line 20. The receivers are connected to a common collection point at combiner 26 with equal length transmission lines 24. The number of receivers is one different than the number of sources.

Sources 16 have operative range 17, receivers 22 have an operative range 23, and sources 16 and receivers 22 combine to have an operative range 17'. In this third embodiment, where the transmitting elements are extended sources and the receiving elements are extended receivers, the width of each source or receiver is 1/(2n·m) of the perimeter of the device on which the source or receiver is mounted along lines 10 and 20, respectively. Thus, where the number of sources (n) is two and the number of receivers (m) is three, the width of each source and receiver is one-twelfth of the perimeter of the device on which the sources or receivers are mounted. Together, the combined operative range 17' between a source and a receiver is one-fourth of the perimeter of the second device.

Figure 6:
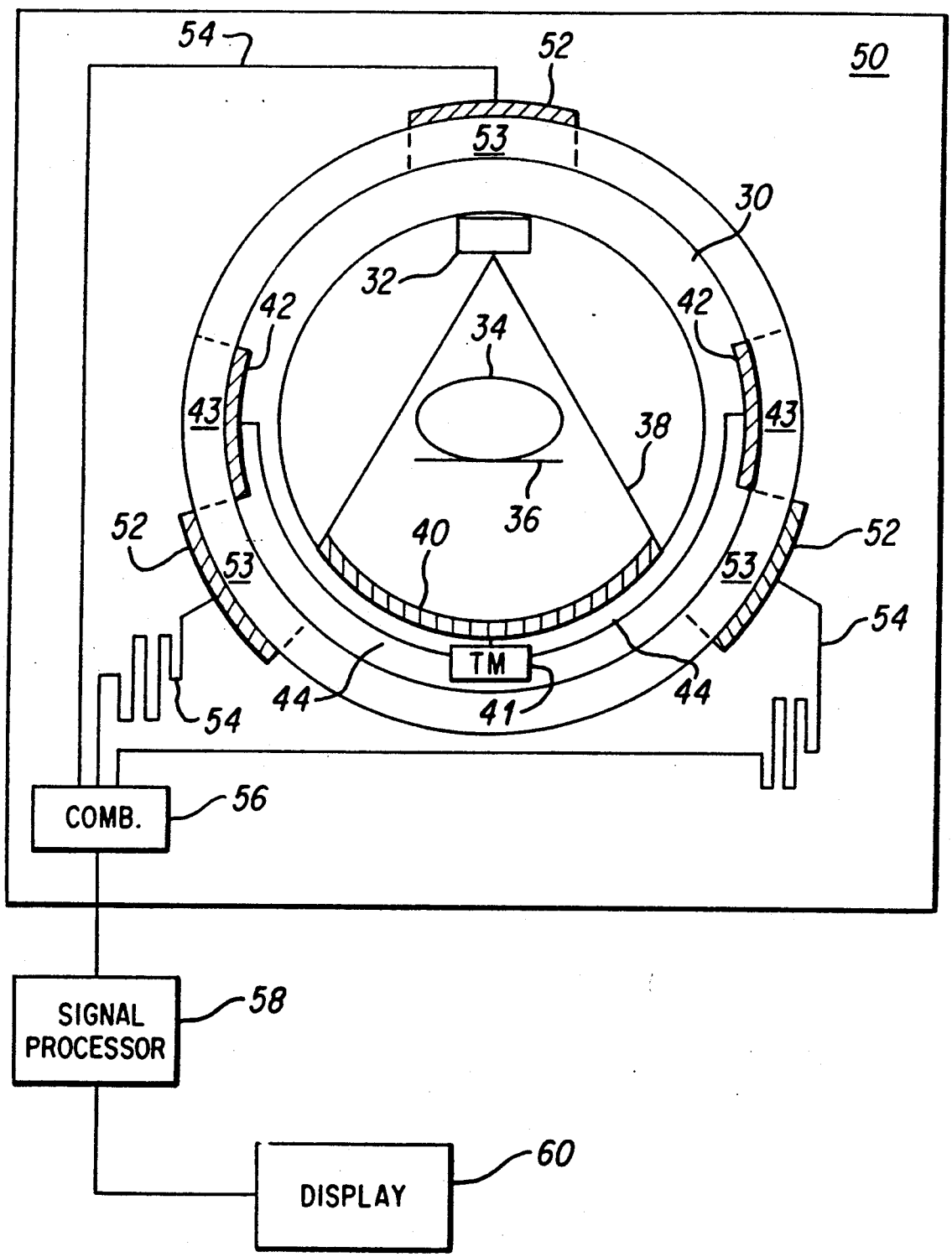
FIG. 6 schematically illustrates a CT scanner incorporating the third embodiment of the invention as shown in FIG. 5.

FIG. 6 schematically illustrates a CT scanner, in which the third embodiment of the invention shown in FIG. 5 is incorporated into a system for communicating data from a rotating frame of a CT scanner to a fixed frame of the CT scanner. A rotating frame 30 is rotatably mounted on a fixed frame 50 and is capable of movement relative to the fixed frame. The rotating frame 30 has a large enough diameter to allow the insertion of the body 34 of a patient to be examined. The patient is supported on a bed 36 or other patient support.

Mounted on the rotating frame is an X-ray source 32 which provides a fan-shaped source of penetrating radiation 38. After passage through the body 34, the X-rays are incident upon a detector 40 opposite the X-ray source 32. The detector may comprise a plurality of detectors of any suitable type such as scintillation crystals with associated photomultipliers or photodiodes.

As embodied herein, a plurality of transmitting elements 42 are mounted equidistant from one another along the outer perimeter of the rotating frame 30. Data collected by the detector is transmitted by transmitter 41 over transmission lines 44 to the transmitting elements 42. Preferably, the transmitting elements 42 are extended optical sources such as infrared laser diodes capable of transmitting the data as infrared light by modulation of intensity or of a carrier by AM, FM, or other well-known methods. The transmitting elements 42 are driven from a common origin at transmitter 41 by transmission lines 44 of equal length from the transmitter 41 to each of the transmitting elements 42. The transmission lines 44 may be electrical or optical transmission lines depending on where electrical-optical conversion takes place.

A plurality of receiving elements are also mounted equidistant from one another along the inner perimeter of fixed frame 50. Preferably, the receiving elements 52 are extended optical receivers such as photodetectors capable of receiving the data transmitted as infrared light. The receiving elements 52 are connected to a common collection point at combiner 56 by equal length transmission lines 54. The transmission lines 56 may be optical or electrical transmission lines depending on where optical-electrical conversion takes place. The output of combiner 56 is connected to a signal processor 58, which is connected to a display unit 60. The data obtained from the detector 40 is manipulated in a known way in the signal processor to produce an image on the display unit.

In the embodiment shown in FIG. 6, the number of transmitting elements (n) is two and the number of receiving elements (m) is three. Thus, the number of receiving elements is one different than the number of transmitting elements. As the rotating frame 30 is moved relative to the fixed frame 50, the operative range of at least one of the receiving elements 52 will overlap with the operative range of one of the transmitting elements 42. In this way, at least one transmit-receive pair will always be in an operative relationship for transmitting and receiving data even though the rotating frame 30 and the fixed frame 50 are in relative motion.

The operative range of each transmitting element 42 and receiving element 52 is 1/(2n·m) of the outer perimeter of the rotating frame and the inner perimeter of the fixed frame respectively. Thus, in the embodiment shown in FIG. 6, the operative range 43 of the transmitting elements is one-twelfth of the outer perimeter of the rotating frame and the operative range 53 of the receiving elements is one-twelfth of the inner perimeter of the fixed frame. Together, the combined operative range between a transmitting element and a receiving element is one-fourth of the perimeter of the fixed frame.

Also, because of the equal length transmission lines 44 and 54, and the limited operative ranges of the transmitting elements and receiving elements, the path length from the transmitter 41 to the receiver 58 will vary only minimally with the relative position of the rotating frame 30 and the fixed frame 50, thus reducing phase errors when the data transmission rate is high. Furthermore, no more than two transmit-receive pairs will be operative at any one time, and at those times, the relative phase difference between the two pairs is zero.

Figure 7:
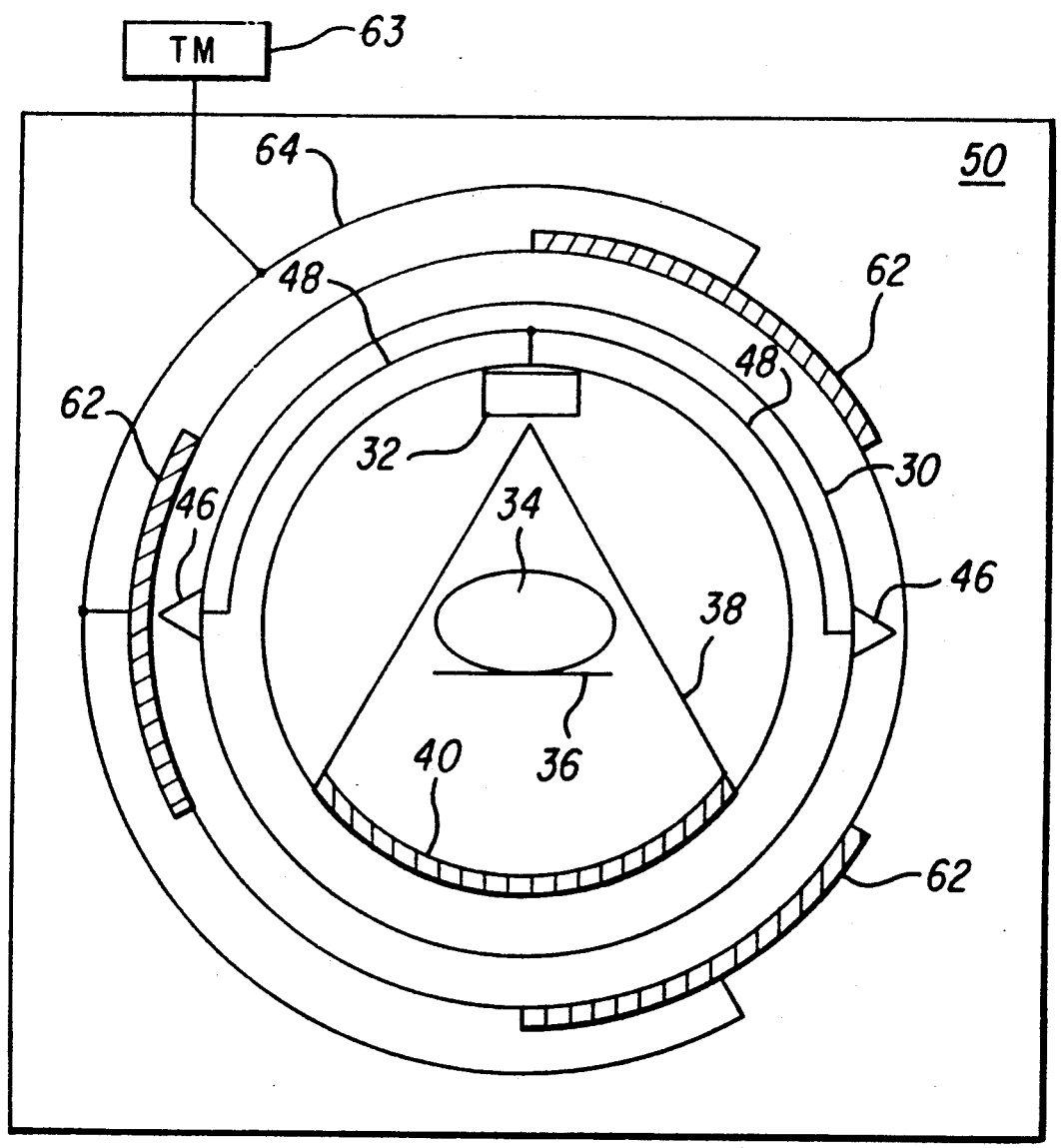
FIG. 7 schematically illustrates a CT scanner incorporating the first embodiment of the invention as shown in FIG. 3.

FIG. 7 schematically illustrates a CT scanner in which the second embodiment of the invention shown in FIG. 4 is incorporated into a system for communicating power from a fixed frame of a CT scanner 50 to a rotating frame 30 of the CT scanner. As embodied herein, a plurality of electrical transmitting elements 62 are mounted equidistant from one another along the inner perimeter of the fixed frame. Preferably, the electrical transmitting elements 62 comprise discrete segments of a high-voltage slip ring. The electrical transmitting elements 62 are driven from a common power source at transmitter 63 by a high-voltage electrical transmission line 64 connected to the electrical transmitting elements 62.

A plurality of electrical receiving elements 46 are also mounted equidistant from one another along the outer perimeter of the rotating frame. Preferably, the electrical receiving elements 46 comprise mechanical brushes that contact the segments of the high voltage slip ring. The electrical receiving elements 46 are connected by a high-voltage electrical transmission line 48 to X-ray source 32 to provide electrical power at a high voltage to operate the X-ray source.

In the embodiment shown in FIG. 7, the number of electrical transmitting elements (n) is three and the number of electrical receiving elements (m) is two. Thus, the number of electrical receiving elements is one different than the number of electrical transmitting elements. As the rotating frame 30 is moved relative to the fixed frame 50, at least one of the plurality of electrical receiving elements 46 will line up with one of the plurality of electrical transmitting elements 62. In this way, at least one transmit-receive pair will always be in an operative relationship for transmitting and receiving electrical power even though the rotating frame 30 and the fixed frame 50 are in relative motion.

The dimension of the electrical transmitting elements 62, which are preferably discrete segments of a high-voltage slip ring, is 1/(n·m) of the inner perimeter of the fixed frame. Thus, in the embodiment shown in FIG. 7, the dimension of the electrical transmitting elements 62 is one-sixth of the inner perimeter of the fixed frame 50.

Another embodiment of the invention is based on the diagram in FIG. 1, where the upper scale may be considered to represent a movable device and the lower scale may be considered to represent a fixed track on which it moves. In this embodiment, there is an indefinitely large number of transmitting (or receiving) elements on the fixed track but still having a definite relationship to the number of receiving (or transmitting) elements on the movable device. The number of elements on the movable device is one different than the number of elements in each length of the fixed track equivalent to the length of the movable device. If either the transmitting or the receiving elements are points, then the other elements shall have an extended operative range of 1/(n·m) of the length of the movable device. If neither the transmitters nor the receivers are points, then each will have operative range of 1/(2n·m) of the length of the movable device.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for communicating energy from a first device to a second device, where the first and second devices are capable of movement relative to one other and include corresponding first and second parallel line segments which pass by one another upon the relative movement of the devices, comprising:
    means for transmitting energy, including a plurality of transmitting elements mounted on the first device equidistant from one another along a first length of the first line segment; and
    means for receiving energy from the transmitting means, including a plurality of receiving elements mounted on the second device equidistant from one another along a second length of the second line segment corresponding to the first length of the first line segment;
    wherein the number of receiving elements is different than the number of transmitting elements, and
    wherein the transmitting elements are point sources, and the receiving elements are extended receivers having a range of operation which is 1/(n·m) of the length of the second line segment, where n is the number of transmitting elements and m is the number of receiving elements, such that the range of operation between a transmitting element and a receiving element is sufficient to assure an operative relationship between at least one of the transmitting elements and one of the receiving elements upon the relative movement of the devices.

2. The system according to claim 1 wherein the number of receiving elements is different from the number of transmitting elements by one.

3. The system according to claim 1 wherein the transmitting elements are driven from a common origin with equal length transmission lines from the origin to each of the transmitting elements, and the receiving elements are connected to a common collection point with equal length transmission lines from each of the receiving elements to the collection point.

4. A system for communicating data from a rotating frame of a CT scanner to a fixed frame of the CT scanner, where the rotating frame and the fixed frame are capable of movement relative to one another, comprising:
    means for transmitting data, including a plurality of transmitting elements mounted equidistant from one another along a perimeter of the rotating frame; and
    means for receiving data from the transmitting means, including a plurality of receiving elements mounted equidistant from one another along a perimeter of the fixed frame corresponding to the perimeter of the rotating frame;
    wherein the number of receiving elements is different than the number of transmitting elements, and
    wherein the transmitting elements have a range of operation which is 1/(2n·m) of the perimeter of the rotating frame, and the receiving elements have a range of operation which is 1/(2n·m) of the perimeter of the fixed frame, where n is the number of transmitting elements and m is the number of receiving elements, such that the range of operation between a transmitting element and a receiving element is sufficient to assure an operative relationship between at least one of the transmitting elements and one of the receiving elements upon relative movement of the fixed frame and the rotating frame.

5. The system according to claim 4 wherein the number of receiving elements is different from the number of transmitting elements by one.

6. The system according to claim 5, wherein the transmitting elements are driven from a common origin with equal length transmission lines from the origin to each of the transmitting elements, and the receiving elements are connected to a common collection point with equal length transmission lines from each of the the receiving elements to the collection point.

7. The system according to claim 4, wherein the transmitting elements are extended optical sources comprising infrared laser diodes capable of transmitting data as infrared light, and the receiving elements are extended optical receivers comprising photodetectors capable of receiving data transmitted as infrared light.

8. The system according to claim 7 wherein the number of recieving elements is different from the number of transmitting elements by one.

9. A system for communicating electrical power from a fixed frame of a CT scanner to a rotating frame of the CT scanner, where the rotating frame and the fixed frame are capable of movement relative to one another, comprising:

means for transmitting electrical power at a high voltage, including a plurality of electrical transmitting elements mounted equidistant from one another along a perimeter of the fixed frame;

means for receiving electrical power at a high voltage from the transmitting means, including a plurality of electrical receiving elements mounted equidistant from one another along a perimeter of the rotating frame corresponding to the perimeter of the fixed frame;

wherein the number of electrical receiving elements is one different than the number of electrical transmitting elements, wherein the electrical transmitting elements comprise discrete segments of a high-voltage slip ring capable of transmitting electrical power at a high voltage, and the electrical receiving elements comprise mechanical brushes capable of receiving power at a high voltage, where at least one of the brushes contacts at least one of the segments, and wherein each of the segments is approximately 1/(n·m) of the perimeter of the fixed frame, where n is the number of electrical transmitting elements and m is the number of electrical receiving elements, such that the range of operation between an electrical transmitting element and an electrical receiving element is sufficient to assure an operative relationship between at least one of the electrical transmitting elements and one of the electrical receiving elements upon the relative movement of the fixed frame and the rotating frame.

10. A system for communicating energy between a first device having a first length and a second device having a second length, where the first device is located on and capable of movement relative to the second device, comprising:

means for transmitting energy, including a plurality of transmitting elements mounted on one of the first and second devices equidistant from one another along its length; and means for receiving energy from the transmitting means, including a plurality of receiving elements mounted on the other of the first and second devices equidistant from one another along its length;

wherein the number of elements on the first device is one different than the number of elements on an equal length of the second device, and wherein the transmitting elements are point sources, and the receiving elements are extended receivers having a range of operation which is 1/(n·m) of the length of the first length, where n is the number of transmitting elements and m is the number of receiving elements, such that the range of operation between a receiving element and a transmitting element is sufficient to assure an operative relationship between one of the transmitting elements and one of the receiving elements upon the relative movement of the devices.

11. A system for communicating energy from a first device to a second device, where the first and second devices are capable of movement relative to one other and include corresponding first and second parallel line segments which pass by one another upon the relative movement of the devices, comprising:

means for transmitting energy, including a plurality of transmitting elements mounted on the first device equidistant from one another along a first length of the first line segment; and means for receiving energy from the transmitting means, including a plurality of receiving elements mounted on the second device equidistant from one another along a second length of the second line segment corresponding to the first length of the first line segment;

wherein the number of receiving elements is different than the number of transmitting elements, and wherein the receiving elements are point receivers, and the transmitting elements are extended transmitters having a range of operation which is 1/(n·m) of the length of the first line segment, where n is the number of transmitting elements and m is the number of receiving elements, such that the range of operation between a transmitting element and a receiving element is sufficient to assure an operative relationship between at least one of the transmitting elements and one of the receiving elements upon the relative movement of the devices.

12. The system according to claim 11 wherein the number of recieving elements is different from the number of transmitting elements by one.

13. The system according to claim 11 wherein the transmitting elements are driven from a common origin with equal length transmission lines from the origin to each of the transmitting elements, and the receiving elements are connected to a common collection point with equal length transmission lines from each of the receiving elements to the collection point.

14. A system for communicating energy from a first device to a second device, where the first and second devices are capable of movement relative to one other and include corresponding first and second parallel line segments which pass by one another upon the relative movement of the devices, comprising:
- means for transmitting energy, including a plurality of transmitting elements mounted on the first device equidistant from one another along a first length of the first line segment; and
- means for receiving energy from the transmitting means, including a plurality of receiving elements mounted on the second device equidistant from one another along a second length of the second line segment corresponding to the first length of the first line segment;
- wherein the number of receiving elements is different than the number of transmitting elements, and
- wherein the transmitting elements are extended sources having a range of operation which is $1/(2n \cdot m)$ of the length of the first line segment, and the receiving elements are extended receivers having a range of operation which is $1/(2n \cdot m)$ of the length of the second line segment, where n is the number of transmitting elements and m is the number of receiving elements, such that the range of operation between a transmitting element and a receiving element is sufficient to assure an operative relationship between at least one of the transmitting elements and one of the receiving elements upon the relative movement of the devices.

15. The system according to claim 14 wherein the number of recieving elements is different from the number of transmitting elements by one.

16. The system according to claim 15 wherein the transmitting elements are driven from a common origin with equal length transmission lines from the origin to each of the transmitting elements, and the receiving elements are connected to a common collection point with equal length transmission lines from each of the receiving elements to the collection point.

17. A system for communicating energy between a first device having a first length and a second device having a second length, where the first device is located on and capable of movement relative to the second device, comprising:
- means for transmitting energy, including a plurality of transmitting elements mounted on one of the first and second devices equidistant from one another along its length; and
- means for receiving energy from the transmitting means, including a plurality of receiving elements mounted on the other of the first and second devices equidistant from one another along its length;
- wherein the number of elements on the first device is one different than the number of elements on an equal length of the second device, and
- wherein the receiving elements are point receivers, and the transmitting elements are extended transmitters having a range of operation which is $1/(n \cdot m)$ of the length of the first device, where n is the number of transmitting elements and m is the number of receiving elements, such that the range of operation between a receiving element and a transmitting element is sufficient to assure an operative relationship between one of the transmitting elements and one of the recieving elements upon the relative movement of the devices.

18. A system for communicating energy between a first device having a first length and a second device having a second length, where the first device is located on and capable of movement relative to the second device, comprising:
- means for transmitting energy, including a plurality of transmitting elements mounted on one of the first and second devices equidistant from one another along its length; and
- means for receiving energy from the transmitting means, including a plurality of receiving elements mounted on the other of the first and second devices equidistant from one another along its length;
- wherein the number of elements on the first device is one different than the number of elements on an equal length of the second device, and
- wherein the transmitting elements are extended sources having a range of operation which is $1/(2n \cdot m)$ of the length of the first length, and the receiving elements are extended receivers having a range of operation which is $1/(2n \cdot m)$ of the first length, where n is the number of transmitting elements and m is the number of receiving elements, such that the range of operation between a receiving element and a transmitting element is sufficient to assure an operative relationship between one of the transmitting elements and one of the receiving elements upon the relative movement of the devices.

* * * * *

UNITED STATES PATENT AND TRADEMARK OFFICE
CERTIFICATE OF CORRECTION

PATENT NO.  :  5,010,254
DATED       :  April 23, 1991
INVENTOR(S) :  John F. Moore It is certified that error appears in the above-identified patent and that said Letters Patent is hereby corrected as shown below:

Claim 1, column 8, line 8, change "other" to --another--.

Claim 8, column 9, line 26, change "recieving" to --receiving--.

Claim 11, column 10, line 25, change "other" to --another--.

Claim 12, column 10, line 55, change "recieving" to --receiving--.

Claim 14, column 10, line 67, change "other" to --another--.

UNITED STATES PATENT AND TRADEMARK OFFICE
CERTIFICATE OF CORRECTION

PATENT NO. : 5,010,254
DATED : April 23, 1991
INVENTOR(S) : John F. Moore

It is certified that error appears in the above-indentified patent and that said Letters Patent is hereby corrected as shown below:

Claim 17, column 12, line 17, change "recieving" to --receiving--.

Signed and Sealed this

Eighth Day of June, 1993

Attest:

Attesting Officer

MICHAEL K. KIRK

Acting Commissioner of Patents and Trademarks